United States Patent [19]
Rootman et al.

[11] Patent Number: 5,857,965
[45] Date of Patent: Jan. 12, 1999

[54] OPERATING STAGE

[75] Inventors: Jack Rootman; Michell D. Visser; Antony J. Hodgson, all of Vancouver; Christian Caritey, Delta, all of Canada

[73] Assignee: The University of British Columbia, Canada

[21] Appl. No.: 78,015

[22] Filed: May 13, 1998

Related U.S. Application Data

[60] Provisional application No. 60/046,946, May 19, 1997.

[51] Int. Cl.$^6$ .................................................. A61B 17/02
[52] U.S. Cl. ........................................... 600/233; 600/208
[58] Field of Search .................................. 600/206, 208, 600/209, 231, 232, 233, 234

[56] References Cited

U.S. PATENT DOCUMENTS

| | | |
|---|---|---|
| 1,839,726 | 1/1932 | Arnold ..................................... 600/233 |
| 2,013,892 | 9/1935 | Lucas ...................................... 600/234 |
| 2,845,925 | 8/1958 | Jayle ...................................... 600/233 |
| 3,970,075 | 7/1976 | Sindelar et al. ........................ 600/231 |
| 4,274,398 | 6/1981 | Scott, Jr. ................................ 600/233 |
| 4,430,991 | 2/1984 | Darnell . | 
| 4,434,791 | 3/1984 | Darnell . |
| 4,457,300 | 7/1984 | Budde .................................... 600/231 |
| 4,510,926 | 4/1985 | Inaba ..................................... 600/231 |
| 4,798,195 | 1/1989 | Seare, Jr. ............................... 600/206 |

*Primary Examiner*—Paul J. Hirsch

[57] ABSTRACT

An operating stage is formed by a rigid ring and is provided with a resilient wedge forming helically wound spring that forms a plurality of resilient pressure applying, suture gripping wedging clamps around the stage and positioned adjacent to the bottom outside corner of the stage.

18 Claims, 6 Drawing Sheets

5,857,965

OPERATING STAGE

This application claims the benefit of U.S. Provisional Application 60/046,946, filed May 19, 1997.

FIELD OF INVENTION

The present invention relates to an operating stage for mounting or connecting retractors, sutures or the like around the periphery of the operating stage.

BACKGROUND OF THE INVENTION

There are numerous different types and forms of operating stages being used by Surgeons to aid in positioning and holding devices such as retractors during operations. They generally take the form of a rigid ring from which various retractors may be mounted using a variety of different connecting devices. These stages are usually mounted on a suitable arm that positions the ring in fixed relation to the operating table or the like on which the patient is positioned.

Retractors are normally mounted on the operating stage or ring by some form of hooking or fixed clamping type mechanism such as a screw clamp that locks the retractor in a fixed position relative to the ring. These clamping devices generally require two hands to operate, one to place the retractor in position in the clamp and the other to screw the clamping mechanism to firmly clamp the retractor in fixed position. Obviously, these systems are inconvenient to use and provide no release to permit relative movement of the retractor and operating stage in the event of an unforeseen relatively high forces that may cause damage to the patient is applied to the retractors.

Also, during many operations, some means must be provided to anchor sutures which are used, in the manner of retractors, for example, to hold back the skin or parts of the body around the operative site. These sutures are generally tied off or weighted off by pinning them to the drapes or by attaching weights or the like; in some cases they are clamped or otherwise connected to the stage.

U.S. Pat. Nos. 4,430,991 and 4,434,791 issued Feb. 14, 1994 and Mar. 6, 1994 respectively, both to Danelle, both show notches on the outside of an operating stage or ring and utilize the notches to receive collapsible tubes and wedge the tubes into position to hold the tubes. One of the ends of each tube is connected to a retractor hook or the like and the wedging action clamps the tube to position the retractors relative to the operating stage.

When sutures are used the sutures pass over the top of the stage or ring before they are clamped into position and thus, tend to limit mobility of the retractors circumferentially around the ring.

BRIEF DESCRIPTION OF THE PRESENT INVENTION

It is an object of the present invention to provide an improved operating stage or ring in which a resilient wedge forming device provides a plurality of clamps to resiliently clamp sutures adjacent to the bottom outside edge of the operating stage so that the sutures may pass beneath the operating stage and still be clamped or held in position.

It is a further object of the present invention to provide a platform that may be releasably clamped to the stage and is movable on tracks circumferentially of the stage to provide a selectively positionable bridge extending over the upper portion of the operating stage.

It is a further object of the present invention to provide a platform for a retractor clamp that uses resilient pressure applied by a pressure member toward a mounting surface of the platform to resiliently squeeze a retractor received there between and wherein the pressure member permits lateral movement of the retractor, i.e. circumferentially to the ring to move the retractor into clamping position.

Broadly, the present invention relates to an operating stage comprising a rigid ring, a resilient wedge forming means defining a plurality of resilient pressure applying, suture gripping wedging clamps, means mounting said resilient wedge forming means on said ring adjacent to a bottom outside portion of said stage to permit access to said suture gripping wedging clamps from beneath said stage.

Preferably, said resilient wedge forming means comprises a helically wound spring having a longitudinal axis deformed to form wedge shaped spaces between adjacent convolutions of said spring, the width of said wedge shaped space diminishing the closer a portion of said wedge shaped space is to the outer periphery of said stage.

Preferably, helically wound spring is formed with discrete spaced segments extending outward from said mounting means substantially around the complete circumference of said ring.

Preferably, said helically wound spring is deformed so that its longitudinal axis has a wave shape with its mid-plane extending substantially parallel to the circumference of the operating stage to form said spaced segments.

Preferably said mounting means comprises a downwardly projecting flange extending at an angle β of between 90 and 30 degrees to a working plane of said stage and said a wave shape and said segments are formed by said helically wound spring passing from one side of said flange to an opposite side of said flange through spaced holes through said flange.

Preferably said angle β is between 60 and 30 degrees to said working plane.

Preferably, said stage further comprises a pair of circumferential grooves extending circumferentially about said ring, one of said grooves opening to an outside peripheral wall of said ring and another of said pair of grooves extending into the inside peripheral wall of said ring, a platform, cooperating flanges on said platform received one in each of said pair of grooves to guide movement of said platform circumferentially around said stage.

Preferably, said platform has a clamping surface, a spring clamp, a clamping element, said spring clamp resiliently biasing said clamping element against said clamping surface of the platform a retractor receiving inlet at one circumferential side of said clamping element so that a retractor may be slid laterally between the clamping element and said clamping surface of the platform into a selected clamped position.

BRIEF DESCRIPTION OF THE DRAWINGS

Further features, objects and advantages will be evident from the following detailed description of the preferred embodiments of the present invention taken in conjunction with the accompanying drawings in which.

DESCRIPTION OF THE PREFERRED EMBODIMENTS

Figure 1:
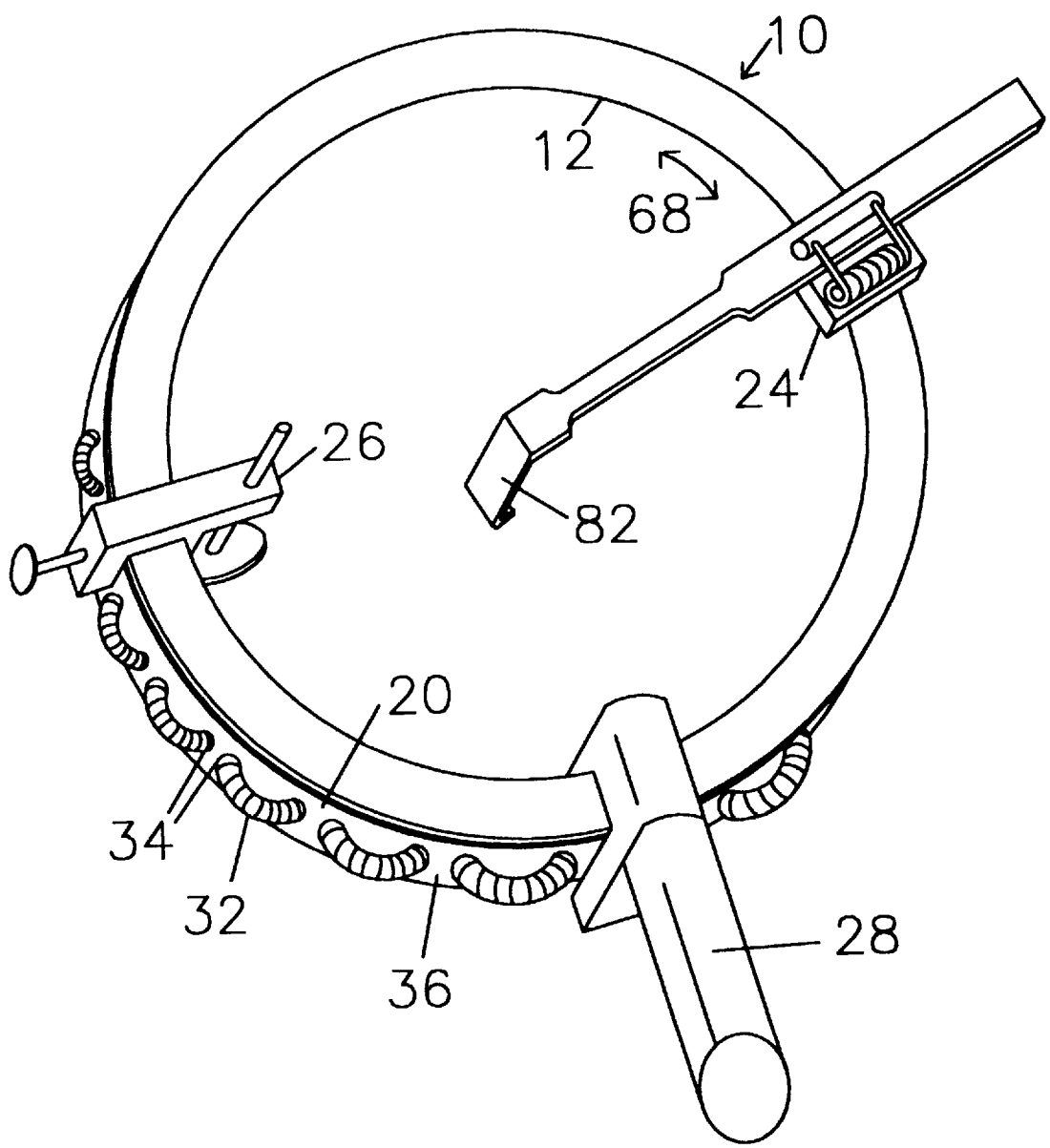
FIG. 1 is an isometric illustration of an operating stage constructed in accordance with the present invention.
Figure 1A:
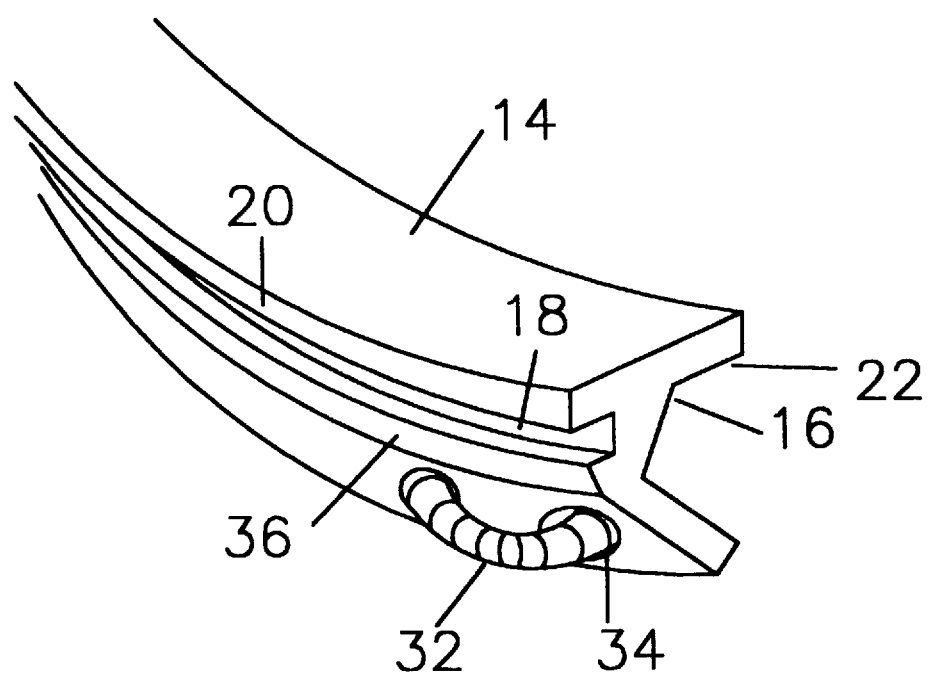
FIG. 1A is a partial section showing a short portion of one embodiment of a helical spring suture clamp.
Figure 2:
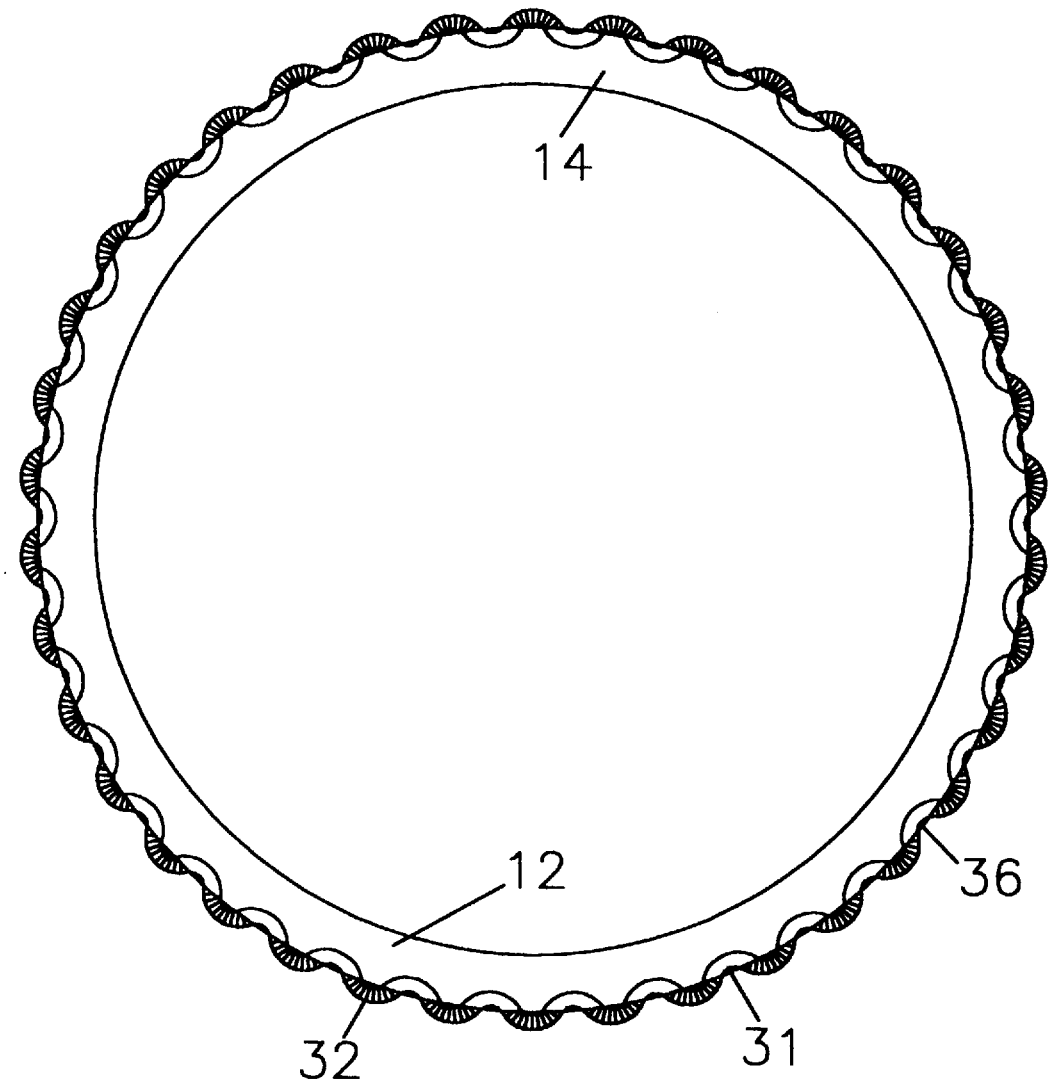
FIG. 2 is a plan view of the operating stage of FIG. 1 showing a resilient suture clamp extending around the full circumference of the stage.

The operating stage or ring 10 as shown in FIGS. 1, 1A and 2 is formed by a ring 12 which in the illustrated arrangement is circular and planer but may be any desired shape e.g. elliptical and may be three dimensional.

Figure 3:
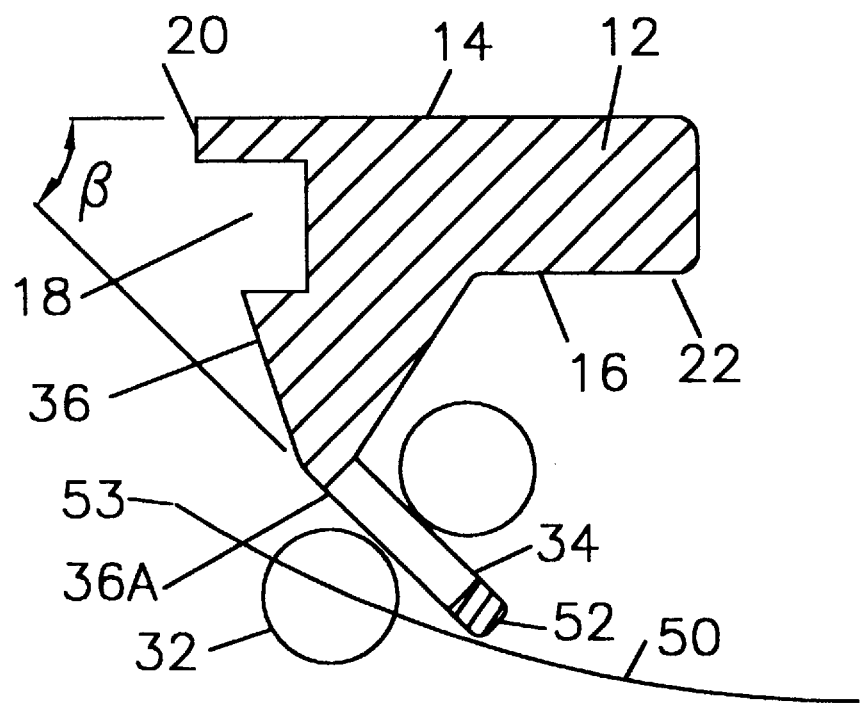
FIG. 3 is a schematic illustration of a section of the stage showing the preferred relative position of the suture clamps.

The ring 12 has an top surface 14 which defines a working plane of the stage and the lower surface 16 and is provided with a circumferential groove 18 extending around the outer wall 20 of the ring 12 (see FIGS. 1A and 3). A second groove or notch 22 is formed at the inner bottom corner of the ring 12. These grooves 20 and 22 are used to mount various mounting or clamping platforms such as the platforms 24 and 26 shown in FIG. 1, as well as for connecting the ring 12 for mounting it from a support arm 28.

Around the outer periphery 36 of the ring below the groove 18 is a suture clamping system formed by a resilient helically wound spring 32. The spring 32 is woven back and forth through spaced holes 34 formed in a mounting flange 36A that extends about the periphery and downward from the outer periphery 36 of the ring 12. The longitudinal centerline 31 (see FIG. 2) of the helically wound spring 32 is deformed to pass back and forth through the spaced holes 34 in the flange 36A. In this arrangement, the spring 32 is positioned below the lower surface 16 of the ring 12, but it may be positioned spaced from the outside wall 20 between the groove 18 and the bottom surface 16 provided it and the suture clamped therein will not interfere with circumferential movement of the platforms 24, 26 and the mounting arms 28 around the ring 12.

The mounting flange 36A may be set at any convenient angle β to the working plane as defined by the top 14 of the ring 12. This angle β will generally be an angle of between 90 and 30 degrees preferably 30 to 60 degrees and most preferred about 45 degrees to facilitate accommodation of the sutures in the spaces between the convolutions which form the resilient wedging clamps for the sutures.

It can be seen from FIGS. 1A, 2, 3, 4 and 5 that the spring 32 is deformed to shape its longitudinal center line 31 essentially in a wave like shape (resembling a sinusoidal shape) by passing outward through one of the holes and then inward through the adjacent hole 34 and outward through the next adjacent hole 34 etc. (see FIG. 4). It will be apparent that the spacing of the holes and the diameter of the spring and the diameter (caliper) of the wire forming the spring 32 combine to define the wedge angle α (see FIG. 4) of the resilient wedge shaped suture clamps formed between adjacent convolutions of the helical spring 32.

In one effective embodiment of the invention the radius of the spring helix, i.e. distance from the axial center line 31 of the spring to the outer edge of the convolutions of the spring 32 may be varied within reasonable limits bearing in mind that intention is to resiliently grip the suture between adjacent convolutions to hold the suture in position during the operation. As an example a helical stainless steel spring made from 0.020 inch diameter 302 stainless steel wire formed into a coil having an outer diameter of 0.12 inches has been found to operate effectively. In a specific application of such a spring the maximum gap between the plate 36 and the adjacent side of the spring 32 was about 0.03 inches.

Figure 4:
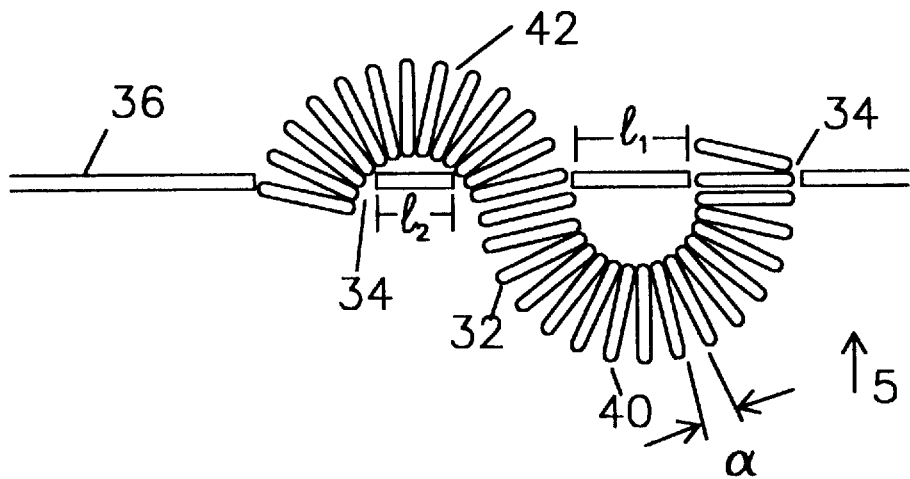
FIG. 4 is an enlarged view of a helical spring forming suture clamp with it longitudinal axis formed into a substantially sinusoidal shape.

In the arrangement illustrated in FIGS. 1A and 4 the spacing between holes 34 through which the helical spring 32 passes to define the spring arches 40 extending outwardly of the ring 12 is longer than the space between the holes 34 through which the helical spring passes toward the center of the ring, i.e. the length L1 is preferably longer than the length L2. By making the length L1 longer than the length L2, the amount of the helical spring exposed, and available to form suture clamps is increased.

It will be apparent that the spacing between holes and the caliper of the wire from which the spring 32 is wound may be varied to produce a selected wedge angle α as desired. The resilience or stiffness of the wire from which the spring 32 is formed, wire diameter of the spring 32 and caliper of the wire together with the spacing of the holes 34 (L1) determine the wedging effect (pressure) of wedge angle α for clamping a suture 50 (see FIG. 3).

Figure 5:
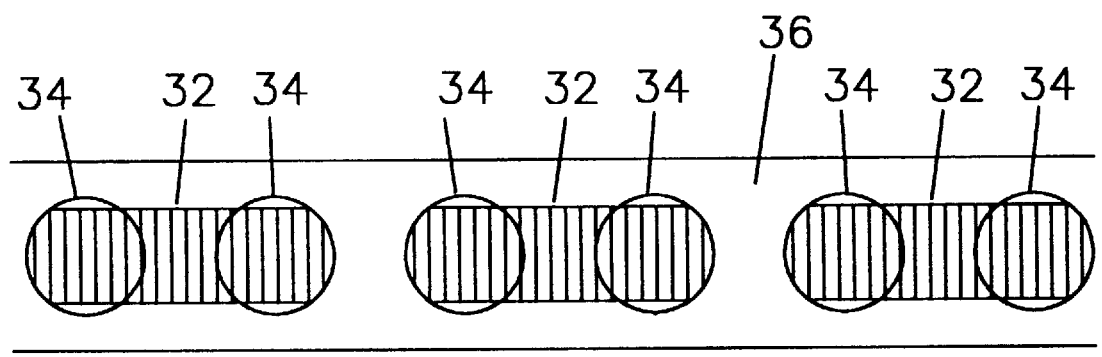
FIG. 5 is a view looking in the direction of the arrow 5 in FIG. 4.

In the embodiment illustrated in FIG. 5 the holes 34 are substantially uniformly spaced regardless of whether adjacent holes 34 so that the outer loops 40 and the inner loops 42 are substantially the same size.

It is preferred that the sutures be received within the wedge angle α formed between adjacent convolutions of the spring 32 to firmly clamp the suture in position and yet with sufficient resilience that the suture may be permitted to slip when excess force is encountered.

While the spring 32 has been shown extending around substantially the full circumference of the stage 10 it will be apparent that discreet circumferentially spaced sections positioned relative to the stage as above described could be used.

In the illustration of FIG. 3, a suture 50 shown in clamp position having a free end 53 and a connected end remote therefrom. The connected end connects the suture to the part to be held (not shown). It will be apparent that the suture extends through the resilient wedging clamp formed by the spring 32 and is held in position preferably with a slight bend in the suture 50 by contact of the suture 50 with the bottom edge 52 of the plate 36. It is not essential that the suture 50 bend around the bottom edge 52.

Figure 6:
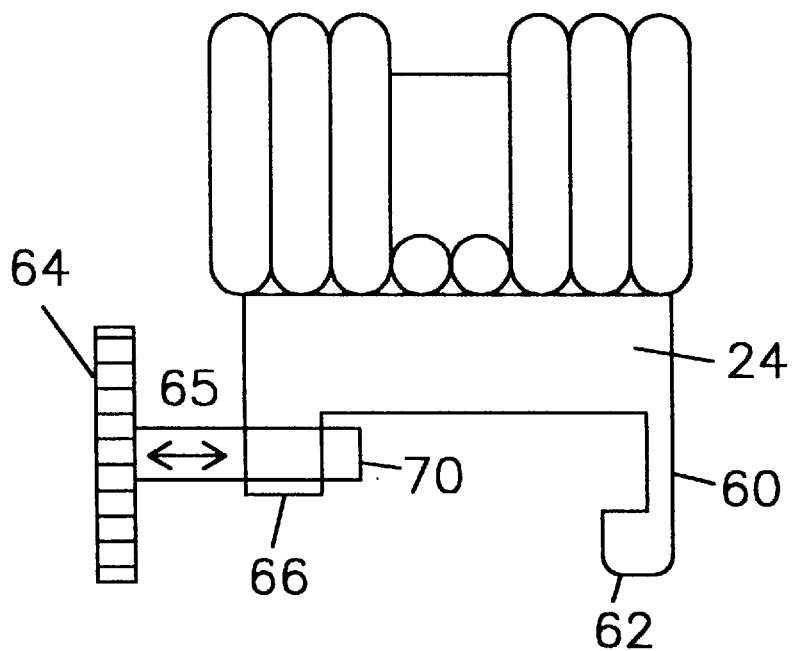
FIG. 6 is a side elevation of the resilient retractor clamp of the present invention.

FIG. 6 shows a typical platform 24 for mounting on the ring 12. In this case, it is formed with a L-shape extension or flange 60 having a free end 62 adapted to be received within the circumferential groove 22 at the bottom inside corner of the plate 12 and with a thumb screw 64 threaded through an arm 66 of the platform 24 adjacent to the outside wall 20 of the ring 12 so that screw 64 may be received in the circumferential groove 18 to hold the platform to the ring 12. The position of the platform 24 may be adjusted as indicated by the arrow 68 and then the screw 64 tightened to clamp the platform 24 in a preset circumferential position relative to the ring 12. The free edge 70 of the thumb screw 64 is received within the groove 18 and to remove the platform 24 from the ring 12 requires that the screw 64 be moved outwardly so that the free end 70 clears the outer wall 20 of the ring 12.

Figure 7:
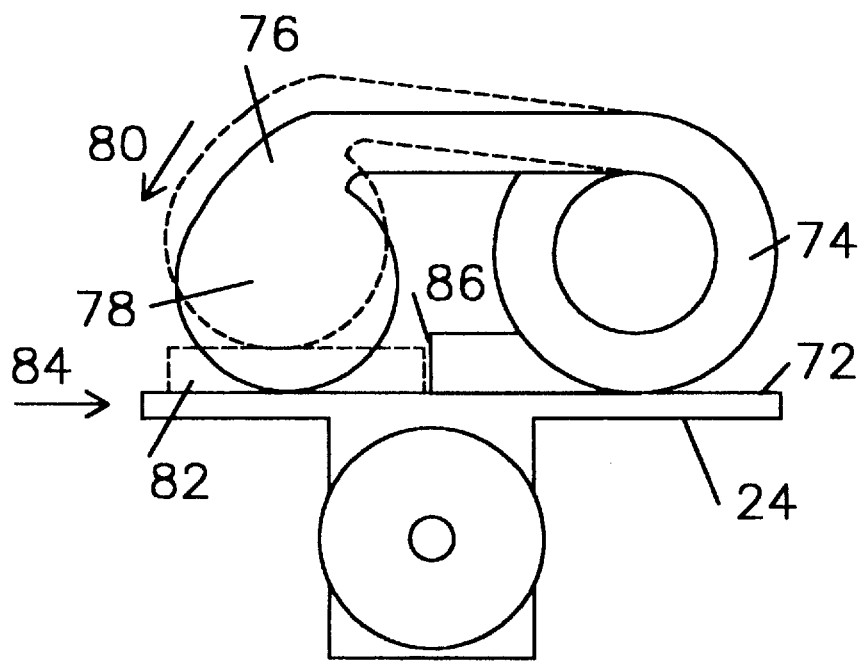
FIG. 7 is an end view of the clamp of FIG. 6 showing a retractor clamped in position.

In the clamp arrangement shown in FIGS. 6 and 7, the platform 24 has an upper clamping surface 72 to which a torsion spring 74 is secured. The torsion spring 74 is provided at its a free end 76 with a pressure member or element 78 that applies a force in the direction of the arrow 80 towards the upper clamping surface 72 of the platform 24. It will be apparent that a retractor such as that shown in the dotted and the dash lines at 82 in FIG. 7 may be forced under the pressure member 78 by movement for example, in the direction of the arrow 84 (e.g. circumferentially of the ring 12) to force the retractor into the clamp through a clamp inlet side of the pressure member 78 and position the retractor 82 between the pressure member 78 and the upper surface 72 of the platform at 24 and thereby clamp the retractor 82 in position. This clamps the retractor 82 in position yet, if undue forces applied to a free end of the retractor, the retractor can slide between surface 72 and the pressure member 78 and release. The amount of pressure necessary to release the retractor is dependent on the retractor thickness and the spring 74 and may be designed for the particular or type of operation with which it is to be used.

Also shown in FIG. 7 is the abutment face 86 which may be used to align the side edge of the retractor 82 substantially radially of the ring 12 or at any other selected direction.

Having described the invention, modifications will be evident to those skilled in the art without departing from the scope of the invention as defined in the appended claims.

We claim:

1. An operating stage comprising a rigid ring, a resilient wedge forming means defining a plurality of resilient pressure applying, suture gripping wedging clamps, means mounting said resilient wedge forming means on said ring adjacent to a bottom outside portion of said stage to permit access to said suture gripping wedging clamps from beneath said stage.

2. An operating stage as defined in claim 1 wherein said resilient wedge forming means comprises a helically wound spring having a longitudinal axis deformed to form wedge shaped spaces between adjacent convolutions of said spring, the width of said wedge shaped space diminishing the closer a portion of said wedge shaped space is to the outer periphery of said stage.

3. An operating stage as defined in claim 2 wherein said helically wound spring is formed with discrete spaced segments extending outward from said mounting means substantially around the complete circumference of said ring.

4. An operating stage as defined in claim 3 wherein said helically wound spring is deformed so that its longitudinal axis has a wave shape with its mid-plane extending substantially parallel to the circumference of the operating stage to form said spaced segments.

5. An operating stage as defined in claim 4 wherein said mounting means comprises a downwardly projecting flange extending at an angle β of between 90 and 30 degrees to a working plane of said stage and said wave shape and said segments are formed by said helically wound spring passing from one side of said flange to an opposite side of said flange through spaced holes through said flange.

6. An operating stage as defined in claim 5 wherein said angle β is between 60 and 30 degrees to said working plane.

7. An operating stage as defined in claim 1 wherein said stage further comprises a pair of circumferential grooves extending circumferentially about said ring, one of said grooves opening to an outside peripheral wall of said ring and the other of said grooves extending into the inside peripheral wall of said ring, a platform, cooperating flanges on said platform received one in each of said pair of grooves to guide movement of said platform circumferentially around said stage.

8. An operating stage as defined in claim 7 wherein said platform has a clamping surface, a spring clamp, a clamping element, said spring clamp resiliently biasing said clamping element against said clamping surface of the platform a retractor receiving inlet at one circumferential side of said clamping element so that a retractor may be slid laterally between the clamping element and said clamping surface of the platform into a selected clamped position.

9. An operating stage as defined in claim 2 wherein said stage further comprises a pair of circumferential grooves extending circumferentially about said ring, one of said grooves opening to an outside peripheral wall of said ring and the other of said grooves extending into the inside peripheral wall of said ring, a platform, cooperating flanges on said platform received one in each of said pair of grooves to guide movement of said platform circumferentially around said stage.

10. An operating stage as defined in claim 9 wherein said platform has a clamping surface, a spring clamp, a clamping element, said spring clamp resiliently biasing said clamping element against said clamping surface of the platform a retractor receiving inlet at one circumferential side of said clamping element so that a retractor may be slid laterally between the clamping element and said clamping surface of the platform into a selected clamped position.

11. An operating stage as defined in claim 3 wherein said stage further comprises a pair of circumferential grooves extending circumferentially about said ring, one of said grooves opening to an outside peripheral wall of said ring and the other of said grooves extending into the inside peripheral wall of said ring, a platform, cooperating flanges on said platform received one in each of said pair of grooves to guide movement of said platform circumferentially around said stage.

12. An operating stage as defined in claim 11 wherein said platform has a clamping surface, a spring clamp, a clamping element, said spring clamp resiliently biasing said clamping element against said clamping surface of the platform a retractor receiving inlet at one circumferential side of said clamping element so that a retractor may be slid laterally between the clamping element and said clamping surface of the platform into a selected clamped position.

13. An operating stage as defined in claim 4 wherein said stage further comprises a pair of circumferential grooves extending circumferentially about said ring, one of said grooves opening to an outside peripheral wall of said ring and the other of said grooves extending into the inside peripheral wall of said ring, a platform, cooperating flanges on said platform received one in each of said pair of grooves to guide movement of said platform circumferentially around said stage.

14. An operating stage as defined in claim 13 wherein said platform has a clamping surface, a spring clamp, a clamping element, said spring clamp resiliently biasing said clamping element against said clamping surface of the platform a retractor receiving inlet at one circumferential side of said clamping element so that a retractor may be slid laterally between the clamping element and said clamping surface of the platform into a selected clamped position.

15. An operating stage as defined in claim 5 wherein said stage further comprises a pair of circumferential grooves extending circumferentially about said ring, one of said grooves opening to an outside peripheral wall of said ring and the other of said grooves extending into the inside peripheral wall of said ring, a platform, cooperating flanges on said platform received one in each of said pair of grooves to guide movement of said platform circumferentially around said stage.

16. An operating stage as defined in claim 15 wherein said platform has a clamping surface, a spring clamp, a clamping element, said spring clamp resiliently biasing said clamping element against said clamping surface of the platform a retractor receiving inlet at one circumferential side of said clamping element so that a retractor may be slid laterally between the clamping element and said clamping surface of the platform into a selected clamped position.

17. An operating stage as defined in claim 6 wherein said stage further comprises a pair of circumferential grooves extending circumferentially about said ring, one of said grooves opening to an outside peripheral wall of said ring and the other of said grooves extending into the inside peripheral wall of said ring, a platform, cooperating flanges on said platform received one in each of said pair of grooves to guide movement of said platform circumferentially around said stage.

18. An operating stage as defined in claim 17 wherein said platform has a clamping surface, a spring clamp, a clamping element, said spring clamp resiliently biasing said clamping element against said clamping surface of the platform a retractor receiving inlet at one circumferential side of said clamping element so that a retractor may be slid laterally between the clamping element and said clamping surface of the platform into a selected clamped position.

\* \* \* \* \*